(12) United States Patent
Eichenberger et al.

(10) Patent No.: US 9,156,771 B2
(45) Date of Patent: Oct. 13, 2015

(54) PROCESS FOR THE PREPARATION OF ENOLATE SALTS OF 4-FLUORO-2-HYDROXYMETHYLENE-3 OXO-BUTYRATES

(75) Inventors: Martina Eichenberger, Brig-Glis (CH); Paul Hanselmann, Brig-Glis (CH); Florencio Zaragoza Dörwald, Visp (CH)

(73) Assignee: LONZA LTD, Visp (CH)

( * ) Notice: Subject to any disclaimer, the term of this patent is extended or adjusted under 35 U.S.C. 154(b) by 112 days.

(21) Appl. No.: 13/809,739

(22) PCT Filed: Jul. 11, 2011

(86) PCT No.: PCT/EP2011/003445
§ 371 (c)(1),
(2), (4) Date: Mar. 20, 2013

(87) PCT Pub. No.: WO2012/007142
PCT Pub. Date: Jan. 19, 2012

(65) Prior Publication Data
US 2013/0338394 A1    Dec. 19, 2013

Related U.S. Application Data

(63) Continuation of application No. 61/364,113, filed on Jul. 14, 2010.

(30) Foreign Application Priority Data

Jul. 13, 2010    (EP) ..................... 10007208

(51) Int. Cl.
| | |
|---|---|
| C07C 51/58 | (2006.01) |
| C07C 51/62 | (2006.01) |
| C07C 67/14 | (2006.01) |
| C07C 67/31 | (2006.01) |
| C07C 67/343 | (2006.01) |
| C07C 69/14 | (2006.01) |
| C07C 69/738 | (2006.01) |

(52) U.S. Cl.
CPC ............ *C07C 67/31* (2013.01); *C07C 51/58* (2013.01); *C07C 51/62* (2013.01); *C07C 67/14* (2013.01); *C07C 67/343* (2013.01); *C07C 69/14* (2013.01); *C07C 69/738* (2013.01)

(58) Field of Classification Search
CPC ........ C07C 51/58; C07C 51/62; C07C 67/14; C07C 67/31; C07C 67/343; C07C 69/14; C07C 69/738
USPC ....................................................... 560/178
See application file for complete search history.

(56) References Cited

U.S. PATENT DOCUMENTS

| | | | |
|---|---|---|---|
| 2,394,255 A | * | 2/1946 | Northey ............ 560/183 |
| 3,637,812 A | * | 1/1972 | Tull et al. ............ 560/181 |
| 5,093,347 A |   | 3/1992 | Graneto et al. |
| 5,616,713 A | * | 4/1997 | Chou et al. .......... 546/250 |
| 2008/0108686 A1 |   | 5/2008 | Gewehr et al. |

FOREIGN PATENT DOCUMENTS

| | | | | |
|---|---|---|---|---|
| EP | 1854788 A1 | | 11/2007 | |
| JP | 01113371 A | | 5/1989 | |
| JP | 08022853 B2 | | 5/1989 | |
| JP | 2004-325727 | * | 11/2004 | ............ G03C 1/498 |
| WO | 2005/123690 A1 | | 12/2005 | |
| WO | 2009/021987 A1 | | 2/2009 | |
| WO | 2009/106619 A1 | | 9/2009 | |

OTHER PUBLICATIONS

Translation of JP2004-325727, Nov. 18, 2004.*
England, "Catalytic Conversion of Fluoroalkyl Alkyl Ethers to Carbonyl Compounds," J. Org. Chem., 49(21), 4007-4008, 1984.*
Fukaya et al., "Facile conversion of perfluoroacyl fluorides into other acyl halides," J. Chem. Soc., Perkin Trans. 1, 1996, 915-920.*
Wald et al., "Trichloroacetatoacetates. I. Synthesis and Reactions of Ethyl and B,B,B-Trifluoroethyl Trichloroacetates," J. Org. Chem., 31(10), 3369-3374, 1966.*
Sharma, "Applications of phase transfer catalysis in the chemical industry, Handbook of Phase Transfer Catalysis," Y. Sasson et al. (Eds.), Chapman and Hall, 1997, pp. 168-199.*
Jones, The Synthesis of Ethyl Ethoxymethyleneoxalacetate and Related Compounds, Journal of the American Chemical Society, 1951, 73(8):3684-3686.
Jones, Organic Compounds of Uranium. V. Derivatives of Uranium (V) Alkoxides, Journal of the American Chemical Society, 78 (1956), S. 6027-6030.
Pryadeina, Synthesis and Structure of 2-Ethoxy- and 2-Aminomethylidene-3-fluoroalkyl-3-oxopropionates, Russian Journal of Organic Chemistry, 2007, vol. 43, No. 7, pp. 951-961.

* cited by examiner

*Primary Examiner* — Paul A Zucker
*Assistant Examiner* — Mark Luderer
(74) *Attorney, Agent, or Firm* — Hoffmann & Baron, LLP

(57) ABSTRACT

Enolate salts of 4-fluoro-2-hydroxymethylene-3-oxobutyrates of formula wherein $R^1$ is $C_{1-10}$ alkyl, $R^2$ and $R^3$ are independently hydrogen or fluorine, M is an alkali or alkaline earth metal, and n is 1 or 2, are prepared from enolate salts of the corresponding 4-fluoro-3-oxobutyrates and carbon monoxide. The enolate salts of formula I can be alkylated or acylated to obtain the corresponding enol ethers and esters. The 4-fluoro-3-oxobutyrate starting material can be prepared from 1,1-difluoroethyl methyl ethers by $SbF_5$-catalyzed fluoromethane elimination followed by halogen exchange with lithium chloride, reacting the thus obtained fluoroacetyl chloride with ketene and quenching with the appropriate alcohol $R^1$—OH.

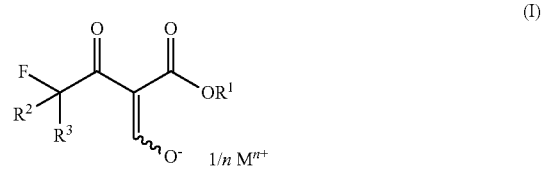

(I)

15 Claims, No Drawings

PROCESS FOR THE PREPARATION OF ENOLATE SALTS OF 4-FLUORO-2-HYDROXYMETHYLENE-3 OXO-BUTYRATES

This application is the U.S. National Phase of, and Applicants claim priority from, International Application No. PCT/EP2011/003445 filed Jul. 11, 2011, U.S. Provisional Application No. 61/364,113 filed Jul. 14, 2010, and European Patent Application No. 10007208.1 filed Jul. 13, 2010, each of which are incorporated herein by reference.

FIELD OF THE INVENTION

The present invention relates to a process for the preparation of enolate salts of 4-fluoro-2-hydroxymethylene-3-oxobutyrates, as well a process for the preparation of enol ethers and enol esters from said enolate salts, and to the enolate salts in solid form. In particular, it relates to a process for the preparation of alkali or alkaline earth enolates of formula

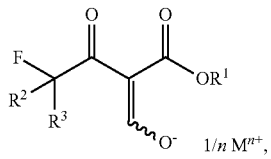

(I)

wherein $R^1$ is $C_{1\text{-}10}$ alkyl, $R^2$ and $R^3$ are independently hydrogen or fluorine, M is an alkali or alkaline earth metal, and n is 1 or 2,
a process for the preparation of enol ethers and enol esters of formula

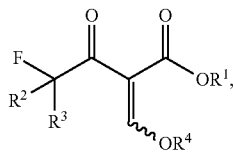

(III)

wherein $R^1$, $R^2$ and $R^3$ are as defined above and $R^4$ is $C_{1\text{-}6}$ alkyl, aryl-$C_{1\text{-}4}$ alkyl, $C_{2\text{-}6}$ alkanoyl or aroyl,
as well as the enolate salts of formula I in solid form.

BACKGROUND OF THE INVENTION

Derivatives of 4-fluoro-2-hydroxymethylene-3-oxobutyrates, in particular the enol ethers of formula III above, wherein $R^4$ is lower alkyl, are valuable intermediates in the synthesis of heterocyclic compounds such as pyrazoles (see e.g. JP 01-113371 A, U.S. Pat. No. 5,093,347, WO 2005/123690 A1). A known synthesis (cf. WO 2005/123690 A1) of said enol ethers is based on the reaction of the corresponding 3-oxobutyrates with trialkyl orthoformates ($HC(OR)_3$), which are relatively expensive, in the presence of acetic anhydride. The orthoformate and acetic anhydride are both used in excess. Moreover, the process suffers from poor atom economy because only one of the three alkoxy groups of the trialkyl orthoformate remains in the product and the other two combine with acetic anhydride to give acetic acid and the corresponding alkyl acetate as byproducts.

Accordingly, it was an object of the present invention to provide an alternative method for the production of the enolates and/or enol ethers or esters of formulae I and III above, which has an improved atom economy and does not require expensive reagents.

SUMMARY OF THE INVENTION

The problem underlying the present invention has been solved by a process, wherein an enolate salt of a 4-fluoro-3-oxobutyrate of formula

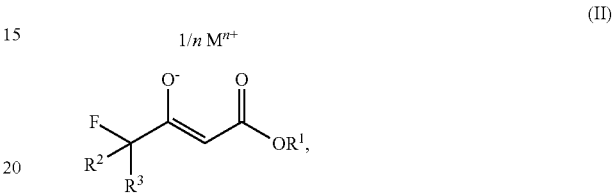

(II)

wherein $R^1$ is $C_{1\text{-}10}$ alkyl, $R^2$ and $R^3$ are independently hydrogen or fluorine, M is an alkali or alkaline earth metal, and n is 1 or 2, is reacted with carbon monoxide to obtain an enolate salt of a 4-fluoro-2-hydroxymethylene-3-oxobutyrate of formula

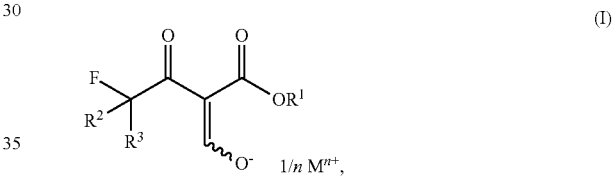

(I)

wherein $R^1$, $R^2$, $R^3$, M and n are as defined above.

Since carbon monoxide is a gas under the reaction conditions, unreacted carbon monoxide can easily be recovered after completion of the reaction. Another advantage of the process according to the invention is the fact that no catalyst is required and no byproducts are formed.

In another embodiment, the enolate salt of formula I, which has been obtained as described above, is further reacted with an alkylating or acylating reagent of formula $$X-R^4 \quad (IV),$$

wherein $R^4$ is selected from the group consisting of $C_{1\text{-}6}$ alkyl, aryl-$C_{1\text{-}4}$ alkyl, $C_{2\text{-}6}$ alkanoyl and aroyl, and X is a leaving group, to give an enol ether or ester of a 4-fluoro-2-hydroxymethylene-3-oxobutyrate of formula

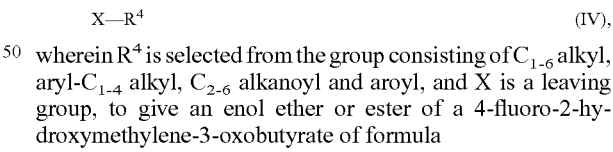

(III)

wherein $R^1$, $R^2$, $R^3$ and $R^4$ are as defined above.

According to the invention, the enolate starting materials of formula II may conveniently be prepared from the corresponding 1,1-difluoroethyl methyl ethers of formula

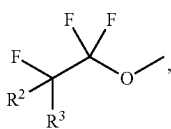

(VI)

wherein $R^2$ and $R^3$ are as defined above, following the steps of
(i) eliminating fluoromethane in the presence of antimony pentafluoride, to obtain an acetyl fluoride of formula

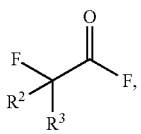

(VII)

wherein $R^2$ and $R^3$ are as defined above,
(ii) reacting said acetyl fluoride (VII) with an alkali or alkaline earth chloride to obtain the corresponding acetyl chloride of formula

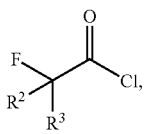

(VIII)

wherein $R^2$ and $R^3$ are as defined above,
(iii) reacting said acetyl chloride (VIII) with ketene ($CH_2=C=O$) to obtain the corresponding acetoacetyl chloride of formula

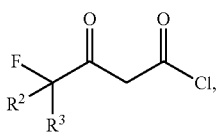

(IX)

wherein $R^2$ and $R^3$ are as defined above, and
(iv) reacting said acetoacetyl chloride (IX) with an alcohol of formula

$R^1$—OH (X), wherein $R^1$ is as defined above, to obtain the 4-fluoro-3-oxobutyrate of formula

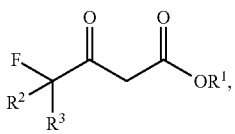

(XI)

or a tautomer thereof,
wherein $R^1$, $R^2$ and $R^3$ are as defined above,
(v) treating said 4-fluoro-3-oxobutyrate of formula XI with a base of formula

$1/n M^{n+} A^-$ (XII), wherein M and n are as defined above and $A^-$ is an anion, preferably selected from the group consisting of $HO^-$, $R—O^-$, $H^-$, and $R^-$, wherein R is $C_{1-6}$ alkyl, to obtain the enolate salt of formula II.

The above process for the preparation of the enolate salts of formula II from the corresponding 1,1-difluoroethyl methyl ethers of formula VI is also an object of the present invention.

The enolate salts of formula I in solid form are likewise an object of the present invention.

DETAILED DESCRIPTION OF THE INVENTION

Here and hereinbelow, the expression "$C_{1-n}$ alkyl" comprises any linear or branched alkyl groups having 1 to n carbon atoms. For example, "$C_{1-10}$ alkyl" comprises groups such as methyl, ethyl, 1-propyl, 1-methylethyl(isopropyl), 1-butyl, 1-methylpropyl(sec-butyl), 2-methylpropyl(isobutyl), 1,1-dimethylethyl(tert-butyl), pentyl, 3-methylbutyl (isopentyl), 1,1-dimethylpropyl(tert-pentyl), 2,2-dimethylpropyl(neopentyl), hexyl, heptyl, octyl, nonyl and decyl. Accordingly, "$C_{1-6}$ alkyl" comprises groups such as methyl, ethyl, 1-propyl, 1-methylethyl, 1-butyl, 1-methylpropyl, 2-methylpropyl, 1,1-dimethylethyl, pentyl, 3-methylbutyl, 1,1-dimethylpropyl, 2,2-dimethylpropyl and hexyl, while "$C_{1-4}$ alkyl" comprises methyl, ethyl, 1-propyl, 1-methylethyl, 1-butyl, 1-methylpropyl, 2-methylpropyl and 1,1-dimethylethyl.

Here and hereinbelow, the expression "aryl-$C_{1-4}$ alkyl" comprises $C_{1-4}$ alkyl groups substituted with one or more aryl groups while the expression "aryl" comprises hydrocarbyl groups containing at least one aromatic ring, such as, for example, phenyl or naphthyl. Non-limiting examples of aryl-$C_{1-4}$ alkyl groups are phenylmethyl(benzyl), diphenylmethyl (benzhydryl), triphenylmethyl(trityl), 2-phenylethyl(phenethyl), 3-phenylpropyl(hydrocinnamyl), 4-phenylbutyl and naphthylmethyl.

The expression "$C_{2-6}$ alkanoyl" comprises acyl group derived from alkanoic acids having 2 to 6 carbon atoms. Examples of $C_{2-6}$ alkanoyl groups are acetyl, propanoyl(propionyl), butanoyl(butyryl), 2-methylpropanoyl(isobutyryl), pentanoyl(valeryl), 2,2-dimethylpropanoyl(pivaloyl) and hexanoyl.

The expression "aroyl" comprises acyl groups derived from arenecarboxylic acids, which may be monocyclic or bi- or polycyclic, and may have substituents such as $C_{1-4}$ alkyl groups or halogens. Examples of aroyl groups are benzoyl, 4-methylbenzoyl(p-toluoyl), 1-naphthoyl and 2-naphthoyl.

Leaving groups are groups which can easily be cleaved in nucleophilic substitution reactions. Examples of suitable leaving groups are halogenides, in particular chloride, bromide or iodide in alkyl, arylalkyl or acyl halogenides, or alkanoates in alkanoic anhydrides, such as acetic anhydride, or sulfates, such as the methyl sulfate or ethyl sulfate anion in dimethyl or diethyl sulfate, or sulfonates, such as the p-toluenesulfonate (tosylate) anion in alkyl p-toluenesulfonates.

Alkali metals are those of the first group of the periodic table of the chemical elements, in particular lithium, sodium, potassium, rubidium and cesium. Alkaline earth elements are those of the second group of the periodic table, in particular magnesium, calcium, strontium and barium. In formulae I and II, n is 1 when M is an alkali metal, and n is 2 when M is an alkaline earth metal.

The reaction of the 4-fluoro-3-oxobutyrate enolate salt (II) with carbon monoxide is advantageously carried out at a temperature in the range of 20 to 80° C.

The carbon monoxide pressure is suitably in the range of 1 to 100 bar ($10^5$ to $10^7$ Pa), preferably in the range of 2 to 50 bar ($2\times10^5$ to $5\times10^6$ Pa), and more preferably in the range of 5 to 20 bar ($5\times10^5$ to $2\times10^6$ Pa).

The reaction with carbon monoxide can be carried out without solvent or in a suitable solvent. Suitable solvents are for example polar solvents such as alcohols, in particular lower alcohols, or esters. Preferred alcohols are those having the formula $R^1$—OH, wherein $R^1$ has the same meaning as in formulae I and II, while preferred esters are the esters derived from said alcohols.

In a preferred embodiment the enolate salt of the 4-fluoro-3-oxobutyrate (II) is prepared in situ from the corresponding 4-fluoro-3-oxobutyrate and a strong base of the corresponding metal M. The strong base can be employed in a stoichiometric amount, it is not necessary to use an excess of base. The strong base may be any strong base that is able to deprotonate the 4-fluoro-3-oxobutyrate, the α-methylene group of which is relatively acidic. Suitable strong bases are for example the hydroxides, hydrides or alkoxides of the alkali and alkaline earth metals or alkali metal alkyls such as methyllithium or butyllithium.

In a more preferred embodiment, the strong base is an alkoxide of formula

$$M^{n+}(OR^1)_n^-  \quad\quad (V)$$

wherein $R^1$, M and n are as defined above.

Most preferably, the metal M is sodium and, consequently, n is 1.

In another preferred embodiment, the substituent $R^1$ in formulae I, II, III and V is $C_{1-4}$ alkyl, most preferably methyl or ethyl.

In still another preferred embodiment, the substituents $R^2$ and $R^3$ in formulae I, II and III are fluorine and hydrogen, respectively.

In the most preferred embodiment, M is sodium, n is 1, $R^1$ is methyl or ethyl, $R^2$ is fluorine, and $R^3$ is hydrogen.

The enolate salt of the 4-fluoro-2-hydroxymethylene-3-oxobutyrate (I) may also exist in other tautomeric forms such as the formyl form depicted below

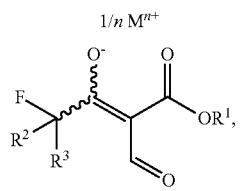

(Ia)

or, if $R^3$ is hydrogen, in one of the dienol forms depicted below:

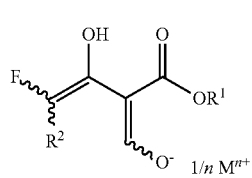

(Ib)

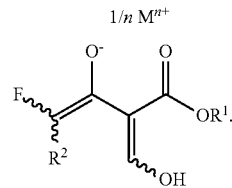

(Ic)

The enolate salt of the 4-fluoro-2-hydroxymethylene-3-oxobutyrate (I) is preferably obtained in solid form, either by conducting the reaction with carbon monoxide without using a solvent or by isolating the enolate salt (I) from its solution in a conventional way, for example by evaporating the solvent or precipitating the product by adding another solvent wherein it is poorly soluble.

In the solid enolate salt of formula I, M is preferably sodium and, consequently, n is 1.

Also preferably, $R^1$ in the solid enolate salt of formula I is $C_{1-4}$ alkyl, more preferably methyl or ethyl.

In another preferred embodiment the substituents $R^2$ and $R^3$ in the solid enolate salt of formula I are fluorine and hydrogen, respectively.

In the most preferred embodiment, M is sodium, n is 1, $R^1$ is methyl or ethyl, $R^2$ is fluorine, and $R^3$ is hydrogen.

The enol ethers or esters of formula III may exist in the depicted keto form or, if $R^3$ is hydrogen, in the tautomeric enol form of formula

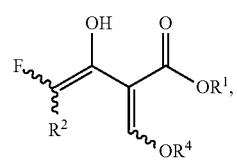

(IIIa)

wherein $R^1$, $R^2$ and $R^4$ are as defined above, or as a mixture of both forms.

Especially preferred enol ethers (III) are those where $R^4$ is $C_{1-4}$ alkyl, in particular methyl. They can be prepared by reacting the enolate salt I with a suitable alkylating agent such as a $C_{1-4}$ alkyl halide or tosylate, in particular a $C_{1-4}$ alkyl bromide or iodide, such as methyl iodide.

Especially preferred enol esters (III) are those where $R^4$ is $C_{2-4}$ alkanoyl, in particular acetyl.

When the enolate starting materials of formula II are prepared from the 1,1-difluoroethyl methyl ethers of formula VI, the antimony pentafluoride in step (i) is advantageously used in catalytic amounts, preferably in an amount of 1 to 5 mol %, based on the amount of 1,1-difluoroethyl methyl ether (VI). The reaction of step (i) may be carried without solvent (neat) or in an inert solvent, such as a haloalkane. The same solvent may also be used in the subsequent steps. Suitable haloalkanes are fluoro- or chloroalkanes, for example dichloromethane or 1,2-dichloroethane. The reaction temperature of step (i) is advantageously in the range of about 0° C. to about 50° C., preferably at room temperature (about 20° C. to about 30° C.). Since the products of step (i), in particular the fluoromethane formed as byproduct, are low-boiling compounds ($CH_3F$: bp=−78° C.), step (i) is advantageously carried out in an autoclave.

The halogen exchange step (step (ii)) in the synthesis of the enolates of formula II may be carried out by simply adding a solid alkali or alkaline earth chloride, preferably lithium chloride, to the acetyl fluoride of formula VII or, preferably, to the reaction mixture obtained in step (i). The reaction temperature in step (ii) is conveniently in the same range as in step (i), preferably at room temperature (about 20° C. to about 30° C.). The amount of alkali or alkaline earth chloride is advantageously 1.0 to 1.2 molar equivalents per mol of 1,1-difluoroethyl methyl ether (VI).

It has been found that the reaction rate can be substantially increased by using a phase transfer catalyst, thus reducing the required reaction time from e.g. about 24 h for lithium chloride without catalyst to about 10 h or less when a catalyst is used. Suitable phase transfer catalysts are those known in the art, for example tetraalkylammonium salts such as tetrabutylammonium chloride. Using a phase transfer catalyst has the advantage that it is also possible to accomplish the halogen exchange with less reactive chlorides such as calcium chloride within a reasonable period of time.

The metal fluoride formed in the halogen exchange step (ii) is advantageously filtered off before isolating the acetyl chloride of formula VIII or, preferably, subjecting the reaction mixture obtained in step (ii) to the reaction with ketene, i.e., step (iii). The ketene is advantageously used in gaseous form, such as the crude (about 70% w/w) ketene gas obtained by pyrolysis of acetic acid. The reaction with ketene may be conducted in the presence of a Lewis acid such as boron trifluoride, but it is also possible to conduct it without addition of a Lewis acid as catalyst. The reaction temperature in step (iii) is advantageously in the range of –50° C. to 0° C. and preferably in the range of –30° C. to –10° C.

The acetoacetyl chloride (IX) obtained in step (iii) or, preferably, the reaction mixture obtained in step (iii) is reacted (quenched) with an alcohol of formula X to obtain the 4-fluoro-3-oxobutyrate of formula XI, which may also be present in the tautomeric enol form depicted below

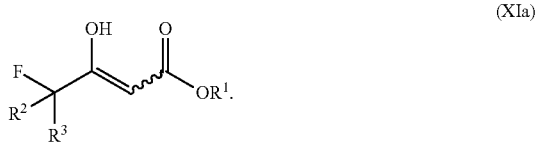

(XIa)

The alcohol is advantageously used in moderate excess, for example about 2 mol per mol of 1,1-difluoroethyl methyl ether (VI) starting material, in order to ensure complete reaction. The reaction with the alcohol is conveniently carried out at a temperature of –30° C. to –10° C., for example at about –15° C.

In a preferred embodiment, the steps (i) to (iv) are conducted without isolating any of the intermediates of formulae VII, VIII and IX.

The 4-fluoro-3-oxobutyrate of formula XI may be isolated and purified according to methods known in the art, for example by evaporating the low-boiling components of the reaction mixture obtained in step (iv), followed by distillation of the thus-obtained crude product.

The enolate salt of formula II is obtained in the conventional way by reacting the 4-fluoro-3-oxobutyrate of formula XI with a strong base of the corresponding metal M, said base having the formula $$1/n M^{n+} A^-$$ (XII), wherein M and n are as defined above and $A^-$ is an anion, preferably selected from the group consisting of $HO^-$, $R—O^-$, $H^-$, and $R^-$, wherein R is $C_{1-6}$ alkyl. Examples of suitable bases are the hydroxides, $C_{1-6}$ alkoxides, hydrides or $C_{1-6}$ alkyls of the alkali or alkaline earth metal M. Preferred alkoxides are those derived from the alcohol $R^1$—OH used in step (iv) above. Suitable metal alkyls are those conventionally used in organic synthesis, such as methyllithium or butyllithium.

The following examples, which however are not intended to limit the scope of the invention, will illustrate in more detail selected embodiments and preferred modes of carrying out the invention.

Example 1

Ethyl 4,4-difluoro-2-hydroxymethylene-3-oxobutyrate, sodium salt (I; $R^1$=Et, $R^2$=F, $R^3$=H, M=Na, n=1)

Ethyl 4,4-difluoro-3-oxobutyrate (234.2 g, 1.41 mol) was dissolved in ethyl acetate (260 g) in an autoclave. Sodium ethoxide (96.0 g, 1.41 mol) was added at 20° C. and the reaction mixture was heated to 60° C. At that temperature, the autoclave was pressurized with carbon monoxide (10 bar). After 5 h the carbon monoxide uptake had ceased and the pressure was released. The solvent was evaporated in vacuo to obtain the desired product as slightly yellow solid.

Yield: 256 g (1.18 mol, 84%).

The product was characterized via $^1H$, $^{13}C$ and $^{19}F$ NMR spectroscopy.

$^1H$ NMR (DMSO-$d_6$, 500 MHz): δ 8.14 (s, 1H), 5.68 (t, $^2J_{H-F}$=58 Hz, 1H), 3.92 (q, $^3J_{H-H}$=7 Hz, 2H), 1.13 (t, $^3J_{H-H}$=7 Hz, 3H).

$^{13}C$ {$^1H$} NMR (DMSO-$d_6$, 125 MHz): δ 175.1 (t, $^2J_{C-F}$=20 Hz), 169.9 (s), 161.8 (s), 113.1 (t, $^1J_{C-F}$=314 Hz), 78.5 (t, $^3J_{C-F}$=2.8 Hz), 59.8 (s), 14.0 (s).

$^{19}F$ NMR (DMSO-$d_6$, 470 MHz): δ-124.3 (d, $^2J_{F-H}$=58 Hz).

Example 2

Ethyl 3-acetoxy-2-(2,2-difluoroacetyl)-acrylate (III; $R^1$=Et, $R^2$=F, $R^3$=H, $R^4$=acetyl)

Mixture of the Keto and Enol Forms

Ethyl-4,4-difluoro-3-oxobutyrate (110.7 g, 0.67 mol) was dissolved in ethyl acetate (115 g) in an autoclave. Sodium ethoxide (45.3 g, 0.67 mol) was added at 20° C. and the reaction mixture was heated to 60° C. The autoclave was then pressurized with carbon monoxide (10 bar) for 5 h. After that time carbon monoxide uptake had ceased and the pressure was released. The reaction mixture was cooled to 0° C. and acetyl chloride (57.5 g, 0.73 mol) was added over 1 h. The reaction mixture was stirred for an additional hour at 30° C. and then filtered to remove NaCl. The filtrate was evaporated in vacuo to obtain the desired product as a colorless liquid. According to $^1H$ NMR data the product was a mixture of ca. 85% enol form (ethyl 3-acetoxy-2-(1-hydroxy-2,2-difluorovinyl)-acrylate) and ca. 15% keto form.

Yield: 125 g (0.53 mol, 79%).

The product was characterized via $^{19}F$, $^1H$ and $^{13}C$ NMR spectroscopy.

$^1H$ NMR (CDCl$_3$, 500 MHz): δ 11.71 (s, 0.85H, enol), 6.55 (t, $^2J_{H-F}$=54 Hz, 0.15H, keto), 5.41 (s, 1H), 4.21-4.14 (m, 2H), 2.42 (s, 3H), 1.26-1.20 (m, 3H).

$^{13}C$ {$^1H$} NMR (CDCl$_3$, 125 MHz): δ 192.1 (t, $^2J_{C-F}$=27 Hz, keto), 171.7 (s), 170.8 (s), 165.5 (s), 164.7 (t, $^2J_{C-F}$=25 Hz, enol), 109.4 (t, $^1J_{C-F}$=242 Hz, keto or enol), 109.3 (t, $^1J_{C-F}$=314 Hz, keto or enol), 91.4 (t, $^3J_{C-F}$=6.0 Hz), 61.1 (s), 21.0 (2 s, keto and enol), 14.0 (2 s, keto and enol).

$^{19}$F NMR (CDCl$_3$, 376 MHz): δ −128.0 (d, $^2J_{F-H}$=54 Hz, keto), −127.9 (d, $^2J_{F-F}$=53.4 Hz, enol), −126.5 (d, $^2J_{F-F}$=53.4 Hz, enol).

Example 3

Ethyl 2-(2,2-difluoroacetyl)-3-methoxyacrylate (III; R$^1$=Et, R$^2$=F, R$^3$=H, R$^4$=OMe)

Mixture of the Keto and Enol Forms

Ethyl-4,4-difluoro-3-oxobutyrate (150 g, 0.90 mol) was dissolved in ethyl acetate (160 g) in an autoclave and treated with sodium ethoxide and carbon monoxide in the same manner as described in Examples 1 and 2. After the CO uptake had ceased, the pressure was released and the reaction mixture was cooled to 0° C. before methyl iodide (128.2 g, 0.90 mol) was added slowly. After stirring for 3 h at 50° C., the reaction mixture was filtered and the filtrate was distilled to remove the ethyl acetate. The product was obtained as a colorless liquid (141 g, 75%).

The product was characterized via $^{19}$F, $^1$H and $^{13}$C NMR spectroscopy. Due to rapid proton exchange the keto-enol tautomery could not be observed in the $^1$H NMR spectrum. According to the $^{19}$F NMR data the product was a tautomeric mixture of ca. 76% enol form and ca. 24% keto form.

$^1$H NMR (DMSO-d$_6$, 500 MHz): δ 6.40 (t, $^2J_{H-F}$=53 Hz, 1H), 4.61 (s, 1H), 3.97 (q, $^3J_{H-H}$=7.1 Hz, 2H), 3.90 (s, 3H), 1.10 (t, $^3J_{H-H}$=7.1 Hz, 3H)

$^{13}$C {$^1$H} NMR (DMSO-d$_6$, 125 MHz): δ 195.9 (t, $^2J_{C-F}$=24 Hz), 175.2 (t, $^2J_{C-F}$=21 Hz), 170.6 (s), 168.3 (s), 114.0 (t, $^1J_{C-F}$=248 Hz), 109.8 (t, $^1J_{C-F}$=247 Hz), 92.0 (s), 58.2 (s), 56.6 (s), 15.6 (s).

$^{19}$F NMR (DMSO-d$_6$, 376 MHz): δ −131.4 (d, $^2J_{F-F}$=52.8 Hz, 0.38F), −131.0 (d, $^2J_{F-F}$=52.8 Hz, 0.38F), −125.0 (d, $^2J_{F-H}$=53 Hz, 0.24F).

Example 4

Ethyl 4,4-difluoro-3-oxobutyrate (XI; R$^1$=Et, R$^2$=F, R$^3$=H)

An autoclave equipped with stirrer, liquid metering pump system and solids-addition device, was charged with 1,2-dichloroethane (187 g) and antimony pentafluoride (2.5 g, 11.4 mmol, 3 mol %) and sealed. The temperature in the autoclave was adjusted to 25° C. and methyl 1,1,2,2-tetrafluoroethyl ether (50 g, 379 mmol) was metered into the closed autoclave. After stirring the reaction mixture at 25° C. for 3 h, solid lithium chloride (17.7 g, 416 mmol) was added. The reaction mixture was stirred for another 24 h and then cooled to 0° C. The autoclave was opened and the reaction mixture was filtrated under nitrogen pressure. The filtrate was transferred into a flask fitted with a gas inlet tube, cooled to −15° C. and BF$_3$-etherate (1.61 g, 11.4 mmol, 3 mol %) was added. To the reaction mixture gaseous ketene (29.6 g, 70% w/w, 493 mmol) obtained by pyrolysis of acetic acid was dosed via the inlet tube within 1 h, before the reaction mixture was quenched with ethanol (34.9 g, 757 mmol) at −15° C. The solvents were removed in vacuo and the crude product was distilled to obtain a colorless liquid.

Yield: 44.0 g (70%)

bp=162° C.

The product was characterized via NMR and GC. According to the $^1$H NMR data the product was a tautomeric mixture of ca. 60% keto form and ca. 40% enol form (ethyl 4,4-difluoro-3-hydroxybut-2-enoate).

$^1$H NMR (CDCl$_3$, 400 MHz): δ 11.76 (s, 0.4H, enol), 6.04 (t, $^2J_{H-F}$=54 Hz, 0.6H, keto), 5.89 (t, $^2J_{H-F}$=54 Hz, 0.4H, enol), 5.48 (s, 0.4H, enol), 4.28-4.20 (m, 2H), 2.28 (s, 1.2H, keto), 1.33-1.26 (m, 3H).

$^{19}$F NMR (CDCl$_3$, 376 MHz): δ −127.6 (d, $^2J_{F-H}$=54 Hz, keto), −129.0 (d, $^2J_{F-H}$=54 Hz, enol).

Example 5

Methyl 4,4-difluoro-3-oxobutyrate (XI; R$^1$=Me, R$^2$=F, R$^3$=H)

The procedure of Example 4 was repeated using methanol instead of ethanol. After distillation the methyl ester was obtained as a colorless liquid. According to the $^1$H NMR data the product was a tautomeric mixture of ca. 60% keto form and ca. 40% enol form (methyl 4,4-difluoro-3-hydroxybut-2-enoate).

Yield: 72%

$^1$H NMR (CDCl$_3$, 500 MHz): δ 11.65 (s, 0.4H, enol), 6.01 (t, $^2J_{H-F}$=54 Hz, 0.6H, keto), 5.88 (t, $^2J_{H-F}$=54 Hz, 0.4H, enol), 5.48 (s, 0.4H, enol), 3.75-3.70 (m, 3H), 2.26 (s, 1.2H, keto).

$^{19}$F NMR (CDCl$_3$, 376 MHz): δ −127.6 (d, $^2J_{F-H}$=54 Hz, keto), −129.0 (d, $^2J_{F-H}$=54 Hz, enol).

Example 6

Ethyl 4,4-difluoro-3-oxobutyrate (XI; R$^1$=Et, R$^2$=F, R$^3$=H)

The procedure of Example 4 was repeated without addition of BF$_3$-etherate. The crude product obtained was analyzed using $^1$H NMR.

Yield: 34 g (54%), besides 6.6 g (14%) ethyl difluoroacetate.

Example 7

Ethyl 4,4-difluoro-3-oxobutyrate (XI; R$^1$=Et, R$^2$=F, R$^3$=H)

The procedure of Example 4 was repeated without addition of BF$_3$-etherate, but the lithium chloride was added together with tetrabutylammonium chloride (10.5 g, 37.9 mmol) as phase transfer catalyst and the reaction time for the halogen exchange was 10 h instead of 24 h.

Yield: 44 g (70%).

The invention claimed is:

1. A process for the production of an enolate salt of a 4-fluoro-2-hydroxymethylene-3-oxobutyrate of formula

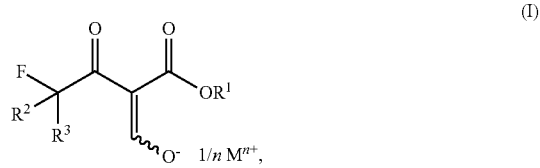

(I)

or a tautomer thereof, wherein R$^1$ is C$_{1-10}$ alkyl, R$^2$ and R$^3$ are independently hydrogen or fluorine, M is an alkali or alkaline earth metal, and n is 1 or 2, comprising the step of reacting a 4-fluoro-3-oxobutyrate enolate salt of formula

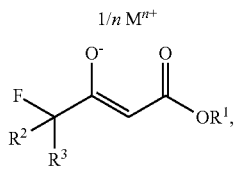
(II)

wherein $R^1$, $R^2$, $R^3$, M and n are as defined above, and/or a tautomer thereof, with carbon monoxide.

2. A process for the production of an enol ether or ester of a 4-fluoro-2-hydroxymethylene-3-oxobutyrate of formula

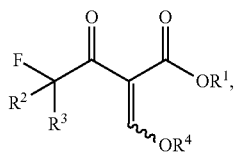
(III)

or a tautomer thereof,
wherein $R^1$, $R^2$ and $R^3$ are as defined in claim 1 and $R^4$ is selected from the group consisting of $C_{1-6}$ alkyl, aryl-$C_{1-4}$ alkyl, $C_{2-6}$ alkanoyl and aroyl, comprising the steps of
(i) providing an enolate salt of formula I according to the process of claim 1, and
(ii) reacting said enolate salt of formula I with an alkylating or acylating reagent of formula $$X-R^4 \quad (IV),$$

wherein $R^4$ is as defined above and X is a leaving group.

3. The process of claim 1 wherein the enolate salt of the 4-fluoro-3-oxobutyrate (II) is prepared in situ from the corresponding 4-fluoro-3-oxobutyrate and a strong base of the corresponding metal M.

4. The process of claim 3, wherein the strong base is an alkoxide of formula $$M^{n+}(OR^1)^-_n \quad (V),$$

wherein $R^1$, M and n are as defined in claim 1.

5. The process of claim 1 wherein M is sodium and n is 1.

6. The process of claim 1 wherein $R^1$ is $C_{1-4}$ alkyl.

7. The process of claim 1 wherein $R^2$ is fluorine and $R^3$ is hydrogen.

8. The process of claim 1 wherein the enolate salt of the 4-fluoro-2-hydroxymethylene-3-oxobutyrate (I) is obtained in solid form.

9. The process of claim 1 wherein the enolate salt of formula II has been synthesized by a process comprising the steps of
(i) eliminating fluoromethane from a 1,1-difluoroethyl methyl ether of formula

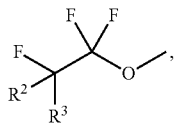
(VI)

wherein $R^2$ and $R^3$ are as defined above, in the presence of antimony pentafluoride, to obtain an acetyl fluoride of formula

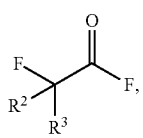
(VII)

wherein $R^2$ and $R^3$ are as defined above,
(ii) reacting said acetyl fluoride (VII) with an alkali or alkaline earth chloride to obtain the corresponding acetyl chloride of formula

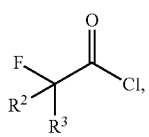
(VIII)

wherein $R^2$ and $R^3$ are as defined above,
(iii) reacting said acetyl chloride (VIII) with ketene ($CH_2=C=O$) to obtain the corresponding acetoacetyl chloride of formula

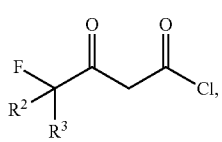
(IX)

wherein $R^2$ and $R^3$ are as defined above, and
(iv) reacting said acetoacetyl chloride (IX) with an alcohol of formula $$R^1-OH \quad (X),$$

wherein $R^1$ is as defined above, to obtain the 4-fluoro-3-oxobutyrate of formula

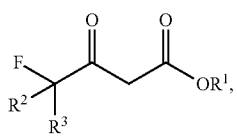
(XI)

wherein $R^1$, $R^2$ and $R^3$ are as defined above, or an enol tautomer thereof, and
(v) treating said 4-fluoro-3-oxobutyrate (XI) with a strong base of formula $$1/n M^{n+} A^- \quad (XII),$$

wherein M and n are as defined above and A⁻ is an anion, preferably selected from the group consisting of HO⁻, R—O⁻, H⁻, and R⁻, wherein R is $C_{1-6}$ alkyl, to obtain the enolate salt of formula II.

10. The process of claim 9, wherein steps (i) to (iv) in the synthesis of the enolate salt of formula II are conducted without isolating the intermediates of formulae VII, VIII and IX.

11. The process of claim 9 wherein step (ii) in the synthesis of the enolate salt of formula II is conducted in the presence of a phase transfer catalyst.

12. A solid enolate salt of a 4-fluoro-2-hydroxymethylene-3-oxobutyrate of formula

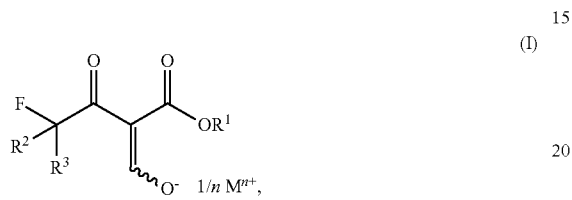

(I)

wherein $R^1$ is $C_{1-10}$ alkyl, $R^2$ and $R^3$ are independently hydrogen or fluorine, M is an alkali or alkaline earth metal, and n is 1 or 2.

13. The solid enolate salt of claim 12, wherein M is sodium and n is 1.

14. The solid enolate salt of claim 12 wherein $R^1$ is $C_{1-4}$ alkyl.

15. The solid enolate salt of claim 12 wherein $R^2$ is fluorine and $R^3$ is hydrogen.

* * * * *